(12) United States Patent
Houben et al.

(10) Patent No.: US 11,007,094 B2
(45) Date of Patent: May 18, 2021

(54) ABSORBENT CORES AND ABSORBENT ARTICLES HAVING ANISOTROPIC FOAM STRUCTURES

(71) Applicants: ONTEX BV, Buggenhout (BE); ONTEX GROUP NV, Erembodegem (BE)

(72) Inventors: Annemie Houben, Ghent (BE); Miguel Angel Rodríguez Pérez, Valladolid (ES); Alberto López Gil, Valladolid (ES); Josias Tirado Mediavilla, Palencia (ES); Javier García González, Valladolid (ES); Lieven Dhooge, Ertvelde (BE); Karen Roets, Goiánia-GO (BR)

(73) Assignees: ONTEX BV, Buggenhout (BE); ONTEX GROUP NV, Erembodegem (BE)

( * ) Notice: Subject to any disclaimer, the term of this patent is extended or adjusted under 35 U.S.C. 154(b) by 0 days.

(21) Appl. No.: 16/647,087

(22) PCT Filed: Sep. 13, 2018

(86) PCT No.: PCT/EP2018/074712
§ 371 (c)(1),
(2) Date: Mar. 13, 2020

(87) PCT Pub. No.: WO2019/053110
PCT Pub. Date: Mar. 21, 2019

(65) Prior Publication Data
US 2020/0214909 A1    Jul. 9, 2020

(30) Foreign Application Priority Data

Sep. 15, 2017   (EP) .................................... 17191491

(51) Int. Cl.
*A61F 13/534*    (2006.01)
*A61F 13/532*    (2006.01)
(Continued)

(52) U.S. Cl.
CPC .......... *A61F 13/534* (2013.01); *A61F 13/532* (2013.01); *A61F 13/15203* (2013.01);
(Continued)

(58) Field of Classification Search
None
See application file for complete search history.

(56) References Cited

U.S. PATENT DOCUMENTS 4,053,341 A * 10/1977 Kleiner .................. B32B 27/00
156/79
5,260,345 A * 11/1993 DesMarais ........ A61F 13/15203
521/148
(Continued)

FOREIGN PATENT DOCUMENTS

DE        19607529 A1    9/1997
EP        2959922 A1    12/2015
(Continued)

OTHER PUBLICATIONS

European Search Report and Written Opinion for European App. No. 17191491.4; dated Feb. 28, 2018.
(Continued)

*Primary Examiner* — Susan S Su
(74) *Attorney, Agent, or Firm* — Vivicar Law, PLLC

(57) ABSTRACT

An absorbent core for an absorbent article, the absorbent core comprising at least two layers, each layer having a width w and a length l along a first plane and a thickness t extending perpendicular thereto, wherein the layers are arranged in facing relationship along the first plane, and wherein the layers comprise a polymeric foam having an
(Continued)

open cell and interconnected porous structure. The first and second layers comprise an anisotropic cell structure having an axis of anisotropy extending substantially parallel to a longest length of a plurality of substantially neighbouring cells. The axis of anisotropy of the second layer extends substantially perpendicular to said thickness t and parallel to said first plane and the axis of anisotropy of the first layer is substantially perpendicular to the axis of anisotropy of the second layer.

22 Claims, 11 Drawing Sheets

(51) Int. Cl.
*A61F 13/15* (2006.01)
*A61F 13/53* (2006.01)
*A61F 13/539* (2006.01)

(52) U.S. Cl.
CPC ............ *A61F 2013/15406* (2013.01); *A61F 2013/15463* (2013.01); *A61F 2013/53081* (2013.01); *A61F 2013/530817* (2013.01); *A61F 2013/53908* (2013.01)

(56) References Cited

U.S. PATENT DOCUMENTS

| | | | |
|---|---|---|---|
| 5,817,704 A * | 10/1998 | Shiveley | A61F 13/53 521/63 |
| 5,856,366 A | 1/1999 | Shiveley et al. | |
| 5,869,171 A | 2/1999 | Shiveley et al. | |
| 6,207,724 B1 | 3/2001 | Hird et al. | |
| 6,245,410 B1 | 6/2001 | Hahnle et al. | |
| 2002/0026977 A1 * | 3/2002 | Mason | B29C 44/468 156/78 |
| 2002/0128338 A1 | 9/2002 | Hird et al. | |
| 2005/0192365 A1 | 9/2005 | Strandburg et al. | |
| 2007/0282025 A1 * | 12/2007 | Collier | C08F 2/32 521/64 |
| 2013/0116646 A1 * | 5/2013 | Robles | A61F 13/472 604/369 |
| 2014/0336606 A1 * | 11/2014 | Bewick-Sonntag | A61F 13/538 604/369 |
| 2017/0119596 A1 * | 5/2017 | Bewick-Sonntag | A61F 13/15203 |
| 2018/0215890 A1 * | 8/2018 | Vo | C08J 9/146 |

FOREIGN PATENT DOCUMENTS

| | | |
|---|---|---|
| WO | 1997032612 A1 | 9/1997 |
| WO | 2008008875 A2 | 1/2008 |

OTHER PUBLICATIONS

International Search Report and Written Opinion for PCT/EP2018/074712, dated Nov. 27, 2018.
Ashida, K. et al., "Isocyanate-Based Foams," In: Landrock, A. H. (Ed.), Handbook of Plastic Foams (New Jersey, Noyes Publications) pp. 13-139 (1995).
Gibson, L.J., et al., "The design of sandwich panels with foam cores," In: Cellular Solids, 2nd ed., Cambridge University Press, pp. 345-386 (1997).
Odian, G., "Polymer blends and interpenetrating polymer networks," In: Principles of Polymerization, 3rd edition, (New York, Wiley-Interscience) pp. 149-150 (1991).
Pinto, J. et al., "Characterization of the cellular structure based on user-interactive image analysis procedures," Journal of Cellular Plastics, 49(6):555-575 (2013).

* cited by examiner

ABSORBENT CORES AND ABSORBENT ARTICLES HAVING ANISOTROPIC FOAM STRUCTURES

CROSS-REFERENCE TO RELATED APPLICATIONS

This application is the national stage application of corresponding international application number PCT/EP2018/074712, filed Sep. 13, 2018, which claims priority to and the benefit of European application no. 17191491.4, filed Sep. 15, 2017, all of which are hereby incorporated by reference in their entirety.

TECHNICAL FIELD

The present invention relates to absorbent cores for use in absorbent articles, preferably of the disposable personal hygiene type, and methods of making the same. Disposable personal hygiene absorbent articles are typically selected from diapers (for baby or adult incontinence), pants (for baby or adult incontinence), sanitary napkins, sanitary towels, light incontinence towels and pads, tampons, and combinations thereof. More preferred absorbent articles herein are selected from sanitary napkins, sanitary towels, light incontinence towels and pads, and combinations thereof.

BACKGROUND

Flexible open-cell polymeric foams are widely used for energy absorption or insulation (thermal, acoustic, mechanical), filtration, absorption of fluids, and the like. In most cases, the foams desired for these purposes have relatively homogeneous structures comprising cells within a given size range joined by open "windows" or "holes" to adjacent cells. Among the various characteristics of such foams that are important for each application are cell size/hole size and distribution, anisotropy, fraction of material in the struts, porosity and properties of the solid phase. In general, work has been devoted to making foams as homogeneous and isotropic as possible with respect to cell size and shape and density.

Polyurethane (PU) foams having a range of densities are known materials. For instance in the Handbook of Polymeric Foams and Foam Technology edited by D. Klempner and K. C. Frisch Hanser, 1991, flexible PU foams with densities from 16 to 150 kg/m3 and used for seating cushioning, carpet underlayment, fabric backing and or insulation and packaging are described. For example, the "integral skin" flexible polyurethane foams have high density skin layers that transition gradually over 1-3 cm into a lower density core region. See for example Ashida, K.; Iwasaki, K. In Handbook of Plastic Foams", Landrock, A. H., ED.; Noyes, 1995; Chapter 2, pp 56, 64-67, incorporated herein by reference. The overall densities of such foams are typically between about 200 and 1,100 $kg/m^3$. These foams do not exhibit distinct regions having different compositional or microstructural properties within a single piece (i.e. they are homogeneous).

Foams may be made from polymer networks which have been entangled to form an interpenetrating network (IPN). IPNs may exhibit some of the properties of both polymer types. See for example Odian, G. G. "Principles of Polymerization", 3rd edition, Wiley-Interscience: New York, 1991, New York, pp 149-150. IPNs do not inherently relate to control over any features at a supramolecular scale (e.g., density or cell size).

Laminates or sandwiches of two or more layers of foams having differing properties are also well known. See for example, Gibson, L. J.; Ashby, M. F. "Cellular Solids" Pergamon Press: Oxford, 1988, Chapter 9. Formation of such composites requires an additional step and may require use of adhesive which may interfere with the functioning or weight of the foam composite and serves as a potential point of failure.

The development of highly absorbent articles for use as disposable diapers, adult incontinence pads and briefs, and sanitary napkins, is the subject of substantial commercial interest. The ability of such products to acquire, distribute, and store fluids such as are found in body exudates (e.g., urine, sweat, feces, and menses) is obviously important to their function. Historically, this has been primarily achieved by using cellulosic fibers and/or superabsorbent particles (generally lightly crosslinked partially neutralized polyacrylic acid that forms a gel when exposed to free water). This approach has, however, encountered a number of difficulties in achieving efficient removal of fluid from the body of the wearer and storage away from the wearer, in part due to the difficulty in controlling and maintaining the appropriate blend of particulate and fiber to provide the desired degree of capillary fluid transport and core integrity and flexibility.

In the past decade intensive research and development has been carried out in the development of foams particularly designed for disposable personal hygiene products, for example as described in U.S. Pat. Nos. 5,817,704, 5,856, 366, 5,869,171, 6,207,724, US2002128338, and US2005192365. All such attempts have focused on optimization of a number of foam properties, such as capillarity, density, cell size and the like, by particular selection of foams, chemical composition and processing techniques.

Although such developments have led to successful commercial products such as Always® Infinity™ (manufactured by the Procter and Gamble Company), a need still exist for further specifically optimizing efficient fast absorption of exudates (like blood, urine, menses etc.) and reduced rewet at a reduced cost. Indeed, some of the disadvantages of foam structures of the prior art include complex processes of making as well as high cost.

The present invention is directed at solving the drawbacks still present in the current state of the art.

SUMMARY OF THE INVENTION

In a first aspect, the present disclosure relates to an absorbent core for an absorbent article, the absorbent core comprising at least two layers, each layer having a width w and a length l along a first plane and a thickness t extending perpendicular thereto, wherein the layers are arranged in facing relationship along the first plane, and wherein at least the second layer 3 comprises an anisotropic cell structure having an axis of anisotropy 5 extending substantially parallel to a longest length of a plurality of substantially neighbouring cells 6, and wherein said axis of anisotropy 5 extends substantially perpendicular to said thickness t and parallel to said first plane.

In a second aspect, the present disclosure relates to an absorbent core for an absorbent article, the absorbent core comprising at least two layers, each layer having a width w and a length l along a first plane and a thickness t extending perpendicular thereto, wherein the layers are arranged in facing relationship along the first plane, and wherein the layers comprise a polymeric foam having an open cell and interconnected porous structure wherein each foam layer comprises an anisotropic cell structure having an axis of anisotropy extending substantially parallel to a longest length of a plurality of substantially neighbouring cells, and wherein the axis of anisotropy of a first layer is substantially perpendicular to the axis of anisotropy of a second layer.

In a further aspect, the present disclosure relates to a process for making absorbent cores described herein comprising the steps of: (i) mixing a formulation comprising a first water based component preferably comprising one or more surfactants, or a first polyol based component and a second isocyanate based component, such that mixture creates a gas phase; (ii) placing said mixture in a mould, preferably the mould comprising a single open end, adapted to promote a substantially unidirectional growth path typically such that cell growth is promoted along an axis crossing said opening during a foaming step to provide a foam comprising an anisotropic cell structure; (iii) demoulding the foam block; (iv) cutting, preferably sequentially, the foam block along a first cutting plane to generate the first layer 2 and a second cutting plane perpendicular to the first cutting plane to generate the second layer 3; (v) optionally repeating step (iv) until substantially the entire foam block is cut into layers; and (vi) assembling the first and second layers 2,3 in facing relationship. Alternatively, the first and second layers are formed by cutting different discrete blocks having the same or different properties (like chemical composition, cell size, porosity and cell shape being anisotropic or isotropic).

In a further aspect, the present disclosure relates to a method of making absorbent articles 7,122 as described herein comprising the steps of: (a) providing an absorbent core as described herein; (b) laminating said absorbent core between a liquid permeable topsheet and a liquid impermeable backsheet, preferably such that the first layer 2 is in direct or indirect contact with the topsheet and the second layer 3 is in direct or indirect contact with the backsheet, typically wherein the first and second layers 2,3 can be adhered together by a bonding substance (typically a substantially hydrophilic bonding substance), such as a hotmelt adhesive or alternatively mechanical bonding such as fusion bonding or ultrasonic bonding. Preferably, and particularly when mechanical bonding is used, the bonding is localized such that less than the entire surface area of contact between the first and second layers is bonded, preferably less than 80%, preferably from 5% to 70%, of said surface area. It is understood herein that alternative methods may be used provided directionality of the cell growth is promoted, for example it is further contemplated herein to use a rotating mould to provide further multiple angled anisotropic orientations rather than bonding different layers together. For example, in an embodiment (not shown) the same steps (i) and (ii) above may be applied, followed by rotation of the mould, after which steps (i) and (ii) above are repeated prior to continuing to demoulding in step (iii).

A preferred aspect of the present disclosure relates to the use of cores as described herein for providing directional flow of menses or urine therethrough and preferably limit the amount of menses residues viewable on the first layer 2 when viewed from the body facing side thereof. This is achieved in a simple and cost effective way without complex and considerable foam formulation and processing requirements. Advantageously, the second layer 3 may be adapted to distribute and retain liquid therein. Typically, at least the second layer is capable of expanding when contacted with a liquid such that the volume thereof in a wet state is greater than the volume thereof in a dry state.

In a further aspect, the disclosure relates to a method of making an absorbent core, the method comprising the steps of: (i) providing a mixture comprising one or more polymers; (ii) placing said mixture in a mould arranged such that cell growth is promoted along an axis, preferably a single axis, during a foaming step to provide a foam comprising an anisotropic cell structure; (iii) forming a foam block by solidifying said mixture; (iv) demoulding the foam block; (v) generating a first layer and/or second layer typically by cutting the foam block along at least one first cutting plane to generate the first layer and/or second layer and preferably a second cutting plane perpendicular to the first cutting plane to generate the second layer and/or first layer; (vi) optionally repeating step (v) until substantially the entire foam block is cut into layers; and (vi) assembling the first and second layers (2,3) in facing relationship.

DETAILED DESCRIPTION OF THE INVENTION

Figure 1:
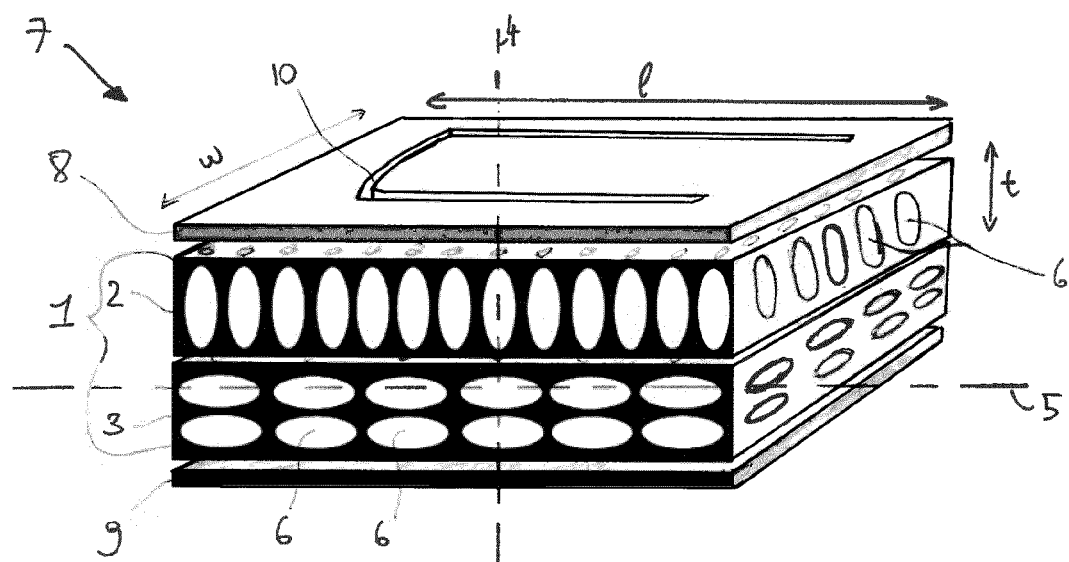
FIG. 1 is a schematic illustration of exemplary absorbent articles herein.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein. Herein, "comprise" and "include" mean that other elements and/or other steps which do not affect the end result can be added. Each of these terms encompasses the terms "consisting of" and "consisting essentially of".

"Anisotropy or anisotropic" as used herein means that the element referred to (e.g. the pores or cells of the foam(s)) are elongate in shape (i.e. have a non-uniform, non-homogeneous or non-spherical shape) and comprise one, preferably only one, longest dimension (i.e. a longest length being greater than all other dimensions forming said element). Preferably, anisotropic elements have an average anisotropy ratio R of greater than 1, as measured according to the method described herein.

"Centerline" as used herein means an imaginary line that is equidistant from lateral surfaces of the element referred to, typically running through said element such to divide said element into two substantially equal halves.

The expression "% by weight" (weight percent or % wt), here and throughout the description unless otherwise defined, refers to the relative weight of the respective component based on the overall weight of the formulation.

The recitation of numerical ranges by endpoints includes all numbers and fractions subsumed within that range, as well as the recited endpoints.

The expression "absorbent article" or "personal hygiene articles" or "personal hygiene absorbent articles" refers to articles which absorb and contain body exudates or discharges such as body fluids, and is intended to include sanitary napkins, pantiliners, diapers, and incontinence pads (and other articles worn in the crotch region of a garment).

The expression "disposable" refers to articles which are intended to be discarded after a single use, composted, or otherwise disposed of in an environmentally compatible manner. (That is, they are not intended to be laundered or otherwise restored or reused as an absorbent article.)

The expression "sanitary napkin" refers to articles which are worn by females adjacent to the pudendal region which are intended to absorb and contain the various exudates which are discharged from the body (e.g., blood, menses, and urine).

The expression "body surface" refers to surfaces of absorbent articles and/or their component members which face the body of the wearer, while the term "garment surface" refers to the opposite surfaces of the absorbent articles and/or their component members that face away from the wearer when the absorbent articles are worn. Absorbent articles and components thereof, including the topsheet, backsheet, absorbent core, and any individual layers of their components, have a body surface and a garment surface.

The expression "substantially parallel" as used herein means that the element referred to is within 30°, preferably within 15°, more preferably within 10°, most preferably within 5°, from the axis, plane or element referred to.

The expression "substantially perpendicular" as used herein means that the element referred to is within 30°, preferably within 15°, more preferably within 10°, most preferably within 5°, from the axis, plane or element referred to.

The expression "substantially neighbouring" as used herein means not necessarily directly neighboring (or in contact) but rather within a given area, preferably of 1.5 mm×1.5 mm, more preferably 1 mm×1 mm, even more preferably 800 µm×800 µm, most preferably 600 µm×600 µm. For sake of clarity, said area being on a plane extending parallel to the longest length of the element referred to.

The "whiteness" of a substrate can be quantified by using the L*, a*, b* value on the CIELAB Colour scale. In short, in this scale the L* value defines the lightness and ranges from 0 to 100, with 0 being absolute black and 100 absolute white. A description of the cielab scale system is presented in details in the experimental section below. The central fluid acquisition zone may in one embodiment have an L* hunter value of at least 90 or higher (for example at least 95, or even at least 97), with the absolute value of each a* and b* being preferably below 1, or even below 0.5 as measured directly on the central fluid acquisition zone of the article. If the central zone has coloured decorations, these values are measured in non-decorated spaces of the central zone.

Figure 7:
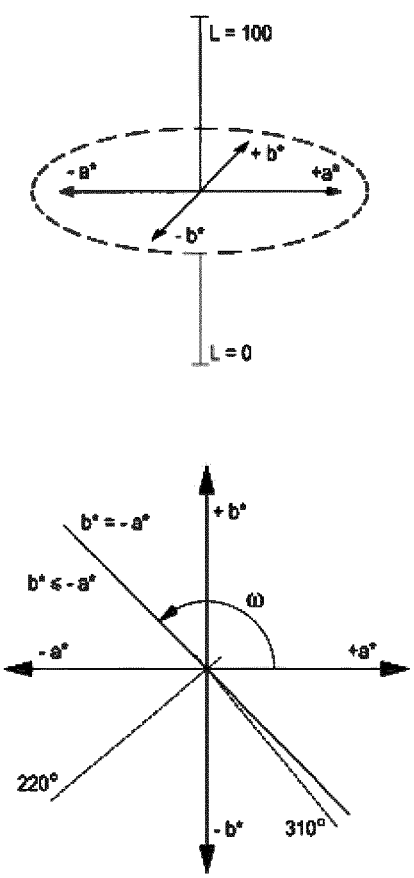
FIG. 7 shows the colour "sphere" used for the representation of colour in the CIELAB system and the horizontal plane of the colour sphere.

The colour of the referred elements (e.g. uppermost surface of first layer of the core) can be characterized by their L*, a* and b* values as measured with the cielab colour scale. It may be preferred that the hue of the colour of the lateral zones may be selected in the blue or green region rather than in the yellow or red region for aesthetic purpose. Furthermore, it has been found that blue and green pigments may better be able to hide underlying stains of blood or urines. Thus the measured a* and b* values may be advantageously such that the relation b*<=−a* is fulfilled. This relation may also be expressed in term of angles values reported to the horizontal colour disc represented on FIG. 7, taking any colour on the +a* axis as having a ω ("omega") angle of 0, any colour on the +b* as having a omega angle of +90° and so forth, and in that case the relation b*<=−a* is equivalent to having a omega angle of from 135° to 315°. It was found that colours in the blue or lilac tone were even more preferable, for which an angle omega of from 220° to 310° is suitable, more precisely of from 257° to 302°.

Absorbent articles suitable for use herein are preferably female personal hygiene articles such as sanitary napkins, typically of the disposable type.

Embodiments of the articles and processes according to the disclosure will now be described. It is understood that technical features described in one or more embodiments may be combined with one or more other embodiments without departing from the intention of the disclosure and without generalization therefrom.

The Absorbent Core

As exemplified in FIG. 1, absorbent cores 1 according to the present disclosure comprise at least two layers 2,3, each layer having a width w and a length l along a first plane and a thickness t extending perpendicular thereto, wherein said layers 2,3 are arranged in facing relationship along said first plane, and wherein said layers 2,3 comprise a polymeric foam having an open cell and interconnected porous structure wherein at least the second layer 3 comprises an anisotropic cell structure having an axis of anisotropy 5 extending substantially parallel to a longest length of a plurality of substantially neighbouring cells 6, and wherein said axis of anisotropy 5 extends substantially perpendicular to said thickness t and parallel to said first plane. It has surprisingly been found that introducing foams with anisotropic cell-shaped properties greatly impacts directionality of capillarity, and by ensuring that the second layer comprises anisotropic cells aligned such that the longest length thereof is generally perpendicular to the liquid flow direction from the first layer into the second layer, a better liquid spreading and utilization of the second layer surface area is achieved.

In an embodiment, this first and second layers have a first and second capillarity respectively, as measured according to the test method described herein, wherein the first and second capillarity are different, preferably wherein the first capillarity is smaller (or less than) the second capillarity. Typically said capillarity being measured in a direction perpendicular to the thickness t and parallel to the first plane.

In a preferred embodiment, each foam layer 2,3 comprises an anisotropic cell structure having an axis of anisotropy 4,5 extending substantially parallel to a longest length of a plurality of substantially neighbouring cells 6, and wherein the axis of anisotropy 4 of a first layer 2 is substantially perpendicular to the axis of anisotropy 5 of a second layer 3. It has surprisingly been found that introducing foams with anisotropic cell-shaped properties greatly impacts directionality of capillarity, and by ensuring that the two layers have perpendicularly oriented anisotropic cells, the exudates are directed in a predetermined manner to directly and quickly flow from the first to the second layer along the thickness direction and once within the second layer quickly spread in the width and length direction. As shown in the examples that follow herein, such brings advantages not only with regards to acquisition time but most importantly excellent resistance to rewet and creation of minimal "blood-spots" on the top surface of the first layer, with the majority of the blood being spread in the second layer which is not viewable by the user when in use. A further advantage is the reduced cost versus foam products specifically designed (e.g. via formulation and the like) for achieving similar high levels of performance. A further advantage is that greater resistance to mechanical compression is achieved when cells are aligned with the longest dimension parallel to the direction of compression and thus aiding to further reduce rewet which generally results from and is exacerbated by highly deforming surfaces upon application of pressure.

In one embodiment, the second layer and/or the first layer have a dry-state stress at 5% strain of greater than 1.5 kPa, preferably from 1.7 to 10 kPa, most preferably from 1.75 to less than 2.15 kPa. The mechanical behaviour of the foams is measured in compression at a strain rate of 10 $s^{-1}$ using an Instron Machine (model 5.500R6025). The samples are prepared by forming cylinders of 50 mm in diameter and 10 mm in thickness. The experiments are conducted at 23±2° C. and 50% relative humidity. The samples are conditioned in these conditions 24 hours prior to the experiments. Without wishing to be bound by theory it is believed that if the resistance to compression is about the same or greater than typical stress at sitting position of a user, a reduced rewetting is achieved.

In one embodiment, the second layer and/or the first layer have a wet-state stress at 5% strain of greater than 1.0 kPa, preferably greater than 1.50 kPa, more preferably from 1.6 to 8 kPa, most preferably from 1.6 to less than 2.0 kPa. The mechanical tests are performed in a similar way to what described in the previous paragraph but in this case prior to the experiments the samples are immersed in artificial blood (as formulated or prepared by SGS Courtray Laboratories (Oignies, France)) for 1 hour to reach full saturation of the foams. The compressive mechanical tests are then performed on fully saturated samples. Similarly, to the above, by ensuring that also in wet-state, the resistance to compression is about the same or greater than typical stress at sitting position of a user, a reduced rewetting is maintained also when the product is saturated with liquids.

Preferably, the first layer 2 is positioned above the second layer 3 such that when said absorbent core 1 is incorporated into an absorbent article, said first layer 2 is closer to a body facing side of the absorbent article than said second layer 3, preferably such that body fluids expelled by a subject first pass through the first layer 2. Such has the advantage of reducing "blood-spots" viewable from the body facing surface.

In an embodiment, the axis of anisotropy 4 of a first layer 2 is substantially perpendicular to the first plane such that said axis 4 crosses said first and second layers 2,3. The axis of anisotropy 5 of a second layer 3 may be substantially parallel to the first plane such that said axis 5 extends along the length l of said second layer 3 without crossing the first layer 2.

Figure 5:
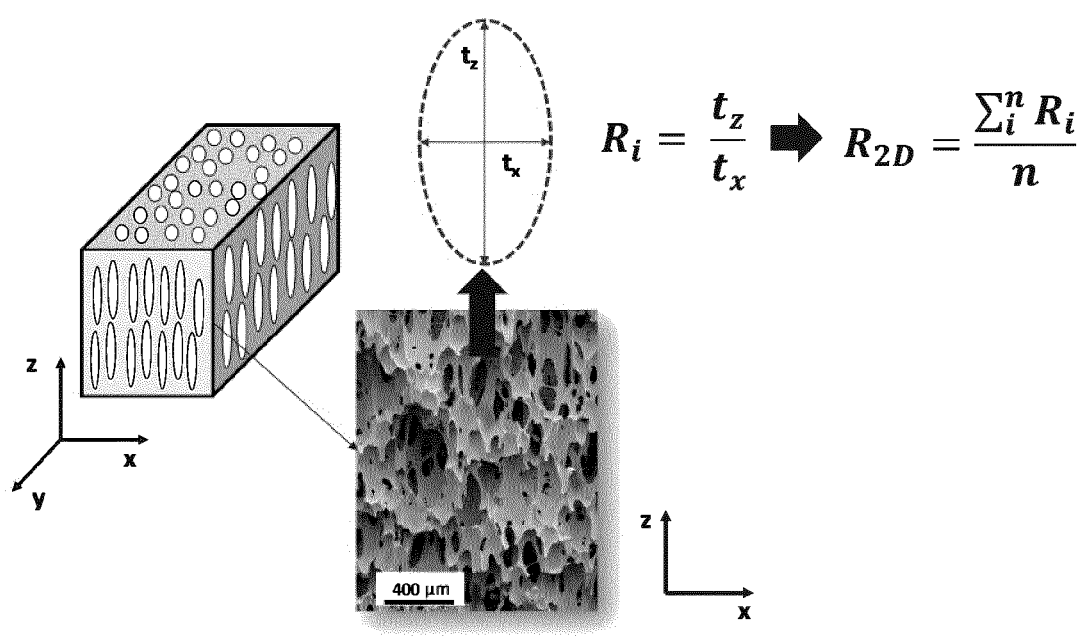
FIG. 5 is an illustration showing how the mean anisotropy ratio R may be determined.
Figure 6:
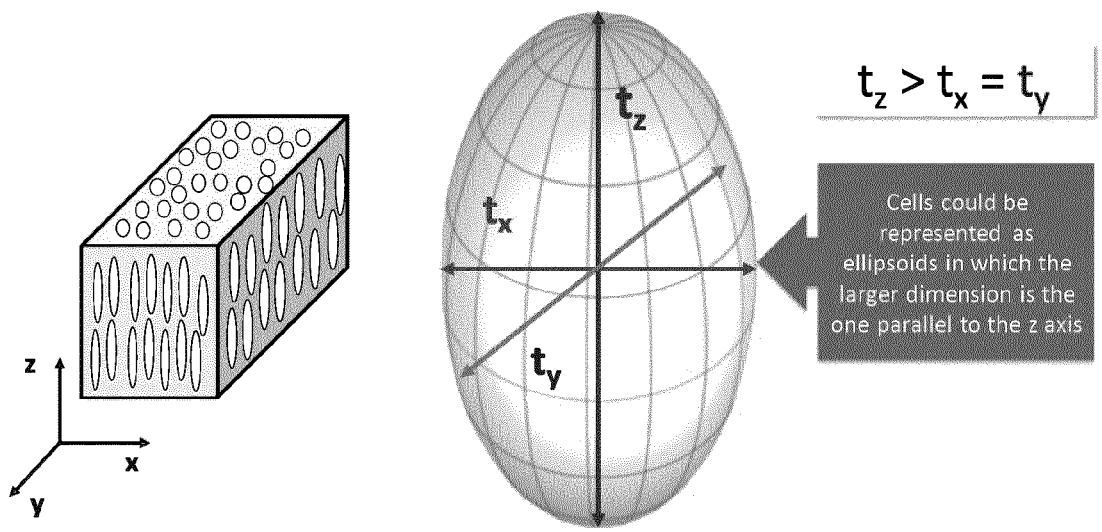
FIG. 6 is an illustration of a typical cell shape of one single cell for a typical foam according to an aspect of the present disclosure.

In a preferred embodiment, the open cells of the foam 6 have an average anisotropy ratio R greater than 1, preferably from 1.1 to 3.5, more preferably from 1.2 to 3.0, more preferably from 1.4 to 3.2, even more preferably from 1.5 to 3.1, even more preferably from 1.6 to 3.0, most preferably from 1.7 to 2.5, as measured according to the method described herein. Preferably the anisotropy ratio R in the ranges described above, is for cells having the longest dimension (or length) extending in a direction substantially parallel to the direction that a fluid is expected to travel through a foam layer comprising said cells (for example, for a foam layer comprising a fluid intake axis parallel to the general direction of fluid transport through said layer, the average anisotropy ratio R described above is taken for cells oriented such that the longest length thereof is substantially parallel to said fluid intake axis). An advantage of such arrangement is that directionality of capillarity is enabled along the longest length of the anisotropic cells. FIG. 5 and FIG. 6 schematically illustrate the shape of such anisotropic cells, wherein in two dimensions (shown in FIG. 5) the anisotropic ratio of each cell is given by dividing the longest cell length $t_z$ by the shortest cell width $t_z$ typically being substantially perpendicular thereto. The average anisotropy ratio R is then given by the sum of said ratios divided by the number of cells n measured. Further details on the method used for calculating the average anisotropy ratio is provided herein below. FIG. 6 illustrates a preferred cell shape, being ellipsoidal in shape and having three dimensions. The longest length $t_z$ being greater than the lengths in directions substantially perpendicular thereto $t_x$ and $t_y$. Preferably, lengths $t_x$ and $t_y$ being substantially equal. An advantage of this arrangement is improved directionality of capillarity. Methods on how to achieve such cell geometry are described herein below in the section pertaining to methods of making.

In an embodiment, the foam comprises, preferably consists of, an open cell hydrophilic polymer foam, more preferably foams selected from the group consisting of polyurethane (PU), poly vinyl alcohol (PVA), polyolefins such as low-density polyethylene (LDPE), ethylene-vinyl acetate (EVA), ethylene butyl acrylate (EBA) (typically that have been modified to improve its hydrophilic character), open cell silicone foams, and mixtures thereof, most preferred being polyurethane foam.

In a preferred embodiment the first layer 2 has a porosity of greater than 70%, preferably greater than 80%, more preferably greater than 90%, even more preferably from 92% to 99%, most preferably from 94% to 98%. In an embodiment, the second layer 3 has a porosity that is less than or equal to that of the first layer 2, preferably the porosity being of greater than 50%, preferably greater than 60%, more preferably greater than 70%, even more preferably from 75% to 95%, more preferably from 76% to 90%. Porosities are measured according to the method described herein.

In a preferred embodiment, and typically irrespective of the actual porosity values described above, the porosity of the second layer 3 is less than the porosity of the first layer 2. An advantage of this embodiment is that compressive strength of the core is guaranteed by the core layer whilst ensuring that the appropriate wicking is achieved.

In an embodiment the average cell size of the first layer 2 is from 50 to 750 microns. In an embodiment, the average cell size of the second layer 3 is from 30 to 500 microns, preferably between 100 to 350 microns. Average cell size is measured according to the method described herein In a preferred embodiment, and typically irrespective of the actual average cell size values described above, the average cell size of the first layer 2 is greater than the average cell size of the second layer 3. An advantage of this embodiment is that wicking along the first plane is further limited in the first layer and rather promoted in the second layer as well as ensuring a faster flow of liquid from the first layer to the second layer, thus ensuring that blood-spots or other stains on the first layer are limited.

In an embodiment (not shown), the average cell size and/or porosity in the first layer exhibit a first gradient in a direction substantially parallel to the anisotropy axis such that respective average cell size and/or porosity proximal to the upper surface of said first layer (closer to the body facing surface) is greater than the average cell size and/or porosity distal from said upper surface and proximal to the second layer. An advantage of said gradient is that further wicking directionality is achieved towards the second layer. Such graded porosity may be achieved for example by using traditional freeze-casting methods as the foaming process whereby the polymer is mixed with a solvent (typically water), then freezed such that the solvent in solidifying forms dendrites that compress and separate the dissolved polymer particles in compacted channels, followed by a sublimation step to remove the solidified solvent and a sintering or curing step to finally form the porous structure. In such process, the porosity and pore/cell size may be controlled by controlling the freezing temperature and cooling position, with the dendritic formation varying as the distance from a cooling position is increased (generally with the low porosities and cell sizes being located close to the cooling position and lower cooling temperatures and higher porosities and cell sizes located distal from said cooling position and higher freezing temperatures). Alternatively, such graded porosity and/or cell size may be achieved by laminating together a plurality of layers having different porosity and/or cell size to form a laminated first and/or second layer having such graded structure and/or by using different formulations of foams that are poured into a mould in a consecutive manner promoting layers with different characteristics.

In an embodiment (not shown), the average cell size and/or porosity in the second layer exhibit a second gradient in a direction substantially parallel to the anisotropy axis such that respective average cell size and/or porosity proximal to a liquid influx point of the second layer is greater than the average cell size and/or porosity at opposing ends of said second layer along said second layer anisotropy axis. The "liquid influx point" being the point at which liquid from the first layer enters the second layer, typically being positioned at about 10% to 30% of the length l of the second layer from the centre of said second layer and in a direction parallel to the anisotropy axis of said layer. Preferably, the direction of the first and second gradients are substantially perpendicular to each other. An advantage of this arrangement is that liquid flow is better promoted from the first layer to the second layer and subsequently, when entering the second layer at the point of influx, is spread laterally across a plane parallel to the first plane in the second layer such to saturate said second layer on the majority of the total surface area of said second layer. Such in turn ensures minimal saturation of the first layer (thus reducing visible stains on the body facing side) and maximizing saturation of the second layer.

In an embodiment, at least one of the foam layers 2,3 described herein has a density p of less than 250 kg/m$^3$, preferably from 15 kg/m$^3$ to 220 kg/m$^3$, more preferably from 20 kg/m$^3$ to 200 kg/m$^3$, even more preferably from 30 kg/m$^3$ to 190 kg/m$^3$. Density is measured using the method described herein.

The Absorbent Article

The absorbent article 7 according to the present disclosure comprises an absorbent core 1 as described herein, preferably wherein the absorbent article 7 comprises a liquid permeable topsheet 8 and a liquid impermeable backsheet 9 with said absorbent core 1 being sandwiched therebetween.

In an embodiment, the topsheet 8 or the uppermost surface of the first layer 2 closest to said topsheet 8 comprises a coloured area comprising a colour pigment imparting a hue having a w angle measured in the CIELAB colour scale of from 135° to 315°, and preferably said coloured area having an opacity of at least 20%, preferably at least 30%, more preferably at least 40%, most preferably at least 50%, as measured according to the method described herein. An advantage of this embodiment is that further masking of the menses residues is achieved thus limiting its viewability from the body facing surface of the article.

Preferably, said coloured area extends through the entire surface of the topsheet 8 or the first layer 2; or is located in a central portion of said absorbent article 7 and distal from perimeter edges thereof, preferably said coloured area being positioned such that when said article 7 is worn by a subject the coloured area is proximal to a genital opening through which body fluids are expelled. An advantage of this embodiment is that the masking effect is localized on where it is needed with this particular construct. Indeed, the cores described herein enable a restricted menses residue spot in the area that comes in close contact with the fluid outlets without substantial propagation or wicking in directions parallel to the first plane, whilst in the second layer (closer to the garment side) wicking in directions parallel to the first plane is promoted to better trap the liquid therein since such layer being on the garment side of the article is not viewable by the user.

In an embodiment, the coloured area is substantially circumscribed by a non-coloured area. This has the advantage of creating a visual perception of performance in the region of typical saturation.

In an embodiment, the absorbent core 1 and/or the topsheet 8, comprises one or more interconnected macro channels 10. Preferably, when the macro channels 10 are located within the absorbent core 1, said macro channels 10 are positioned at least on the upper surface of the first layer 2, said upper surface being opposite the second layer 3, and extending at least a portion of the length l and width w of said first layer 2. The macro channel may form a recess within the first layer 2 having a predetermined depth. By "macro channel" as used herein, it is intended that the channel referred to has a length of greater than 1 cm and a width of greater than 2 mm, and preferably a depth of greater than 0.5 mm. Wherein, the depth is parallel to an axis crossing both the first and second layers and wherein the length and width are along a plane parallel to the first plane. An advantage of this configuration is that liquids (e.g. menses or urine) can more effectively and quickly be distributed over the absorbent core and also to account for deformation of the foam upon swelling in wet conditions so as to retain its general overall shape and limit excess deformation that could lead to discomfort when worn by a subject.

In a preferred embodiment, the one or more macro channels are interconnected such that liquid is distributed therethrough without liquid build-up. Preferably, substantially the entire channel surface is colored (with a color different from the rest of the absorbent core) and exhibits the Opacity levels described in the above paragraphs. An advantage of this arrangement is to provide masking of stains in the location where most needed, as well as providing a perception of added depth and absorption of the product.

Figure 2:
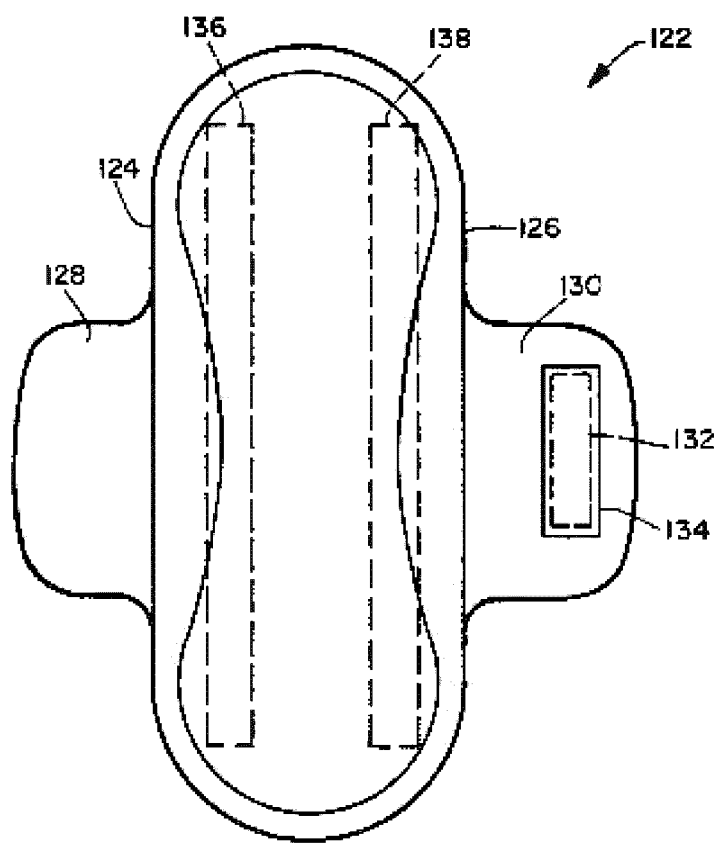
FIG. 2 is a top plan view of a disposable absorbent article, a sanitary napkin, which is one embodiment of the present disclosure.

FIG. 2 is a top plan view of a further exemplary embodiment of a disposable absorbent article 122 (more particularly a sanitary napkin) which is one preferred embodiment of the present disclosure. The absorbent article typically comprises a liquid impermeable backsheet having a garment facing side and a body facing side opposite thereto, a liquid permeable topsheet positioned on the body facing side of the backsheet, and an absorbent core positioned between the backsheet and the topsheet. The absorbent core may comprise a foam structure as described herein, and may further comprise cellulosic fibers and/or super absorbent polymer particles. The core may further comprise a nonwoven (or tissue paper) wrap that encloses said foam, fibers and/or particles therein. The absorbent article 122 may further comprise opposed side edges 124, 126 extending substantially parallel to a longitudinal length of the absorbent article 122 that are typically perpendicular to a width of the absorbent article. Optionally, the absorbent article 122 may comprise one or more wings 128, 130 on at least a portion of each of the side edges 124, 126.

The absorbent article 122 may further comprise one or more first adhesive regions 136, 138 on the garment facing side of the backsheet that typically extend along the length of the absorbent article 122. Such first adhesive regions may be adapted to adhere to a wrap sheet arranged to form a pouch enclosing the absorbent article 122 and after removal of said wrap sheet adhere to a garment surface of the underwear of the wearer. Optionally, when the absorbent article comprises one or more wigs 128, 130, each said wing 128, 130 may comprise a second adhesive region 132 on the garment facing side and arranged to adhere to a garment surface of the wearer. In this embodiment, the absorbent article 122 comprises at least one (preferably two) protective strip 134 over the second adhesive region 132 to prevent it from adhering to the wrap sheet forming the pouch enclosing the absorbent article 122 when in the pre-use folded position (i.e. in the individually wrapped state prior to use/opening).

In an alternative embodiment (not shown), the absorbent article may be a tampon, a pant or a diaper (whether for babies or adult incontinence).

The Process of Making

The method of making absorbent cores 1, as described herein, generally comprises the steps of: (i) providing a mixture comprising one or more polymers; (ii) placing said mixture in a mould and applying one or more fluid substances (typically a gas) such to promote a non-uniform cell growth that typically leads to an anisotropic cell structure (this is preferably achieved by using a mould with a single open end such that cell growth is promoted along an axis crossing said opening during a foaming step to provide a foam comprising an anisotropic cell structure, typically having an anisotropic axis extending through said opening). It is however understood that other methods my equally be used in order to achieve such non-uniform cell growth without departing from the teaching of the present disclosure); (iii) forming a foam block by solidifying said mixture; (iv) demoulding the foam block; (v) cutting the foam block along at least one first cutting plane to generate a first layer 2 and/or second layer 3, and preferably a second cutting plane perpendicular to the first cutting plane to generate the second layer 3 and/or first layer 2; (vi) optionally repeating step (v) until substantially the entire foam block is cut into layers; and (vi) assembling the first and second layers 2,3 in facing relationship.

In an embodiment, the process for making absorbent cores described herein comprises the steps of: (i) mixing a formulation comprising a first water based component preferably comprising one or more surfactants, or a first polyol based component and a second isocyanate based component, such that mixture creates a gas phase; (ii) placing said mixture in a mould having a single open end such that cell growth is promoted along an axis crossing said opening during a foaming step to provide a foam comprising an anisotropic cell structure; (iii) demoulding the foam block; (iv) optionally cutting, preferably sequentially, the foam block along a first cutting plane to generate the first layer 2 and a second cutting plane perpendicular to the first cutting plane to generate the second layer 3; (v) optionally repeating step (iv) until substantially the entire foam block is cut into layers; and (vi) assembling the first and second layers 2,3 in facing relationship.

In an embodiment (not shown), the first and second layers are joined together by fusion bonding. Preferably, "fusion bonding" as used herein comprises the steps of wetting a joining surface of the first and/or second layer (typically with one or more solvents) followed by placing said joining surfaces of the first and second layers together and applying a drying step such to bond the first and second layers together. Preferably, pressure is applied in an effective amount such to force at least some of the first layer into the second layer (and/or vice versa) prior to the drying step. More preferably said fusion bonding is applied only to a portion of the total joining surface area of the first and second layers, typically less than 80%, preferably from 5% to 70% of said joining surface. An advantage is that a strong bonding is achieved with limited compromise to fluid flowability between layers.

Figure 3:
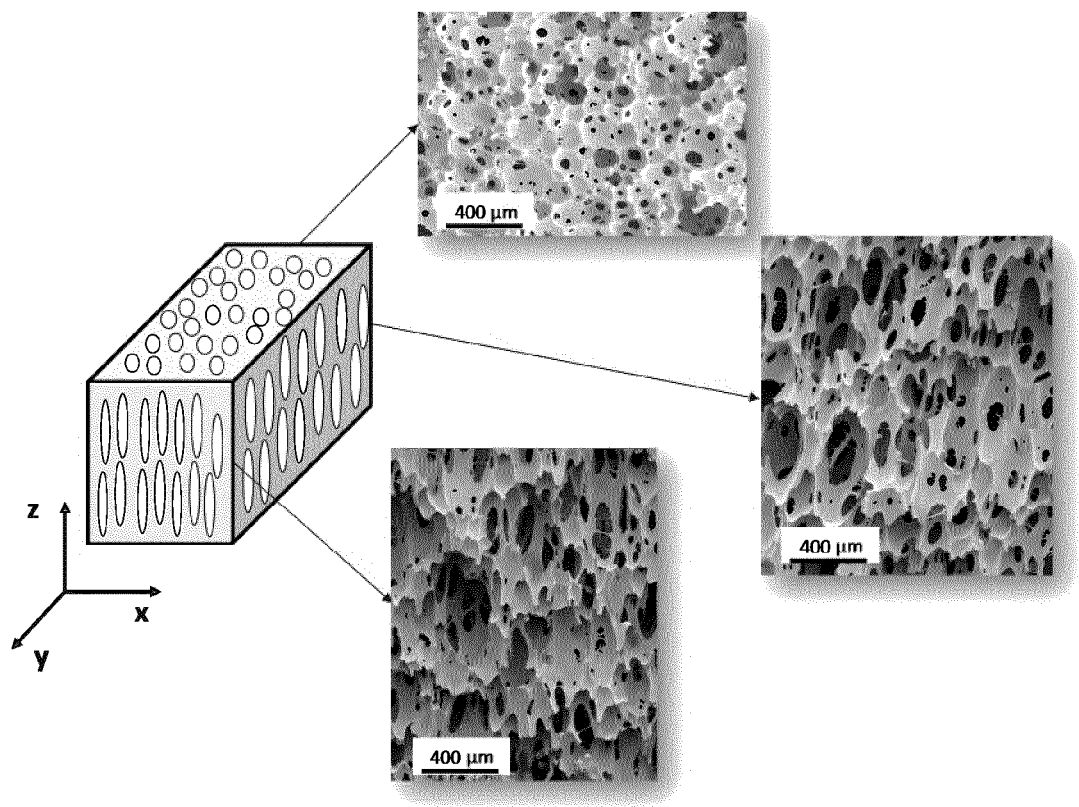
FIG. 3 is a schematic representation, including exemplary SEM images, shown in three planes of an open cell foam block according to an embodiment of the present disclosure.

FIG. 3 shows schematically (and further with Scanning Electric Microscope (SEM) images) the cells structures obtained by following the above method. As can be observed, the controlled cell growth in one direction ensures that the resulting foam blocks have isotropic shaped cells in planes parallel to the x-y plane and anisotropic shaped cells in planes parallel to the z-x plane and z-y plane.

Figure 4:
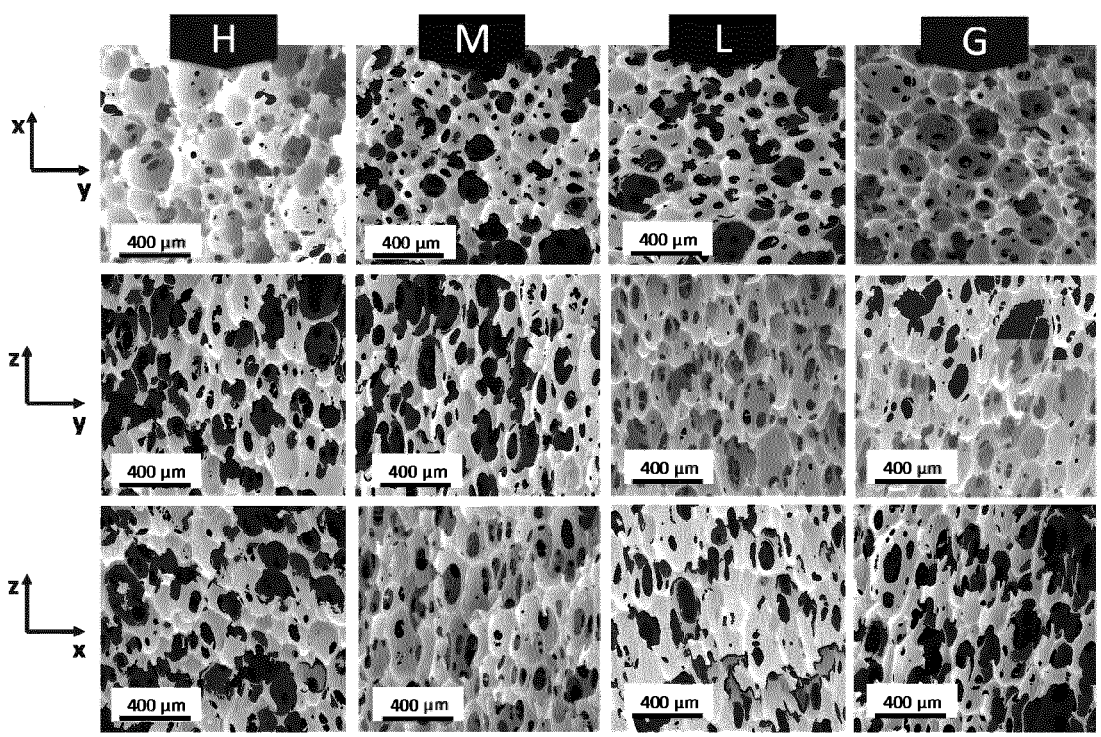
FIG. 4 SEM images taken from some exemplary foams according to an aspect of the disclosure showing different cellular structures in different planes.

FIG. 4 shows schematically (and further with SEM images) different cell shapes for different foams obtained at the various indicated planes of the respective foam blocks. As can be observed from the images, the method described herein is consistent in providing foam blocks having isotropic shaped cells in the x-y plane and anisotropic shaped cells in the z-x and z-y planes. Cell size and anisotropy ratio can be controlled by different approaches. Cell size can be modified by using nucleating agents, and the type and amount of surfactant and/or modifying the mixing conditions of the reactants. Anisotropy ratio can be controlled by modifying the viscosity of the initial materials and/or the relative speed of the blowing and gelling reactions and/or the cell nucleation mechanisms, all being common in the art of foam making. It is understood that such parameters may be changed according to the desired needs without departing from the teaching of the present disclosure.

Figure 8:
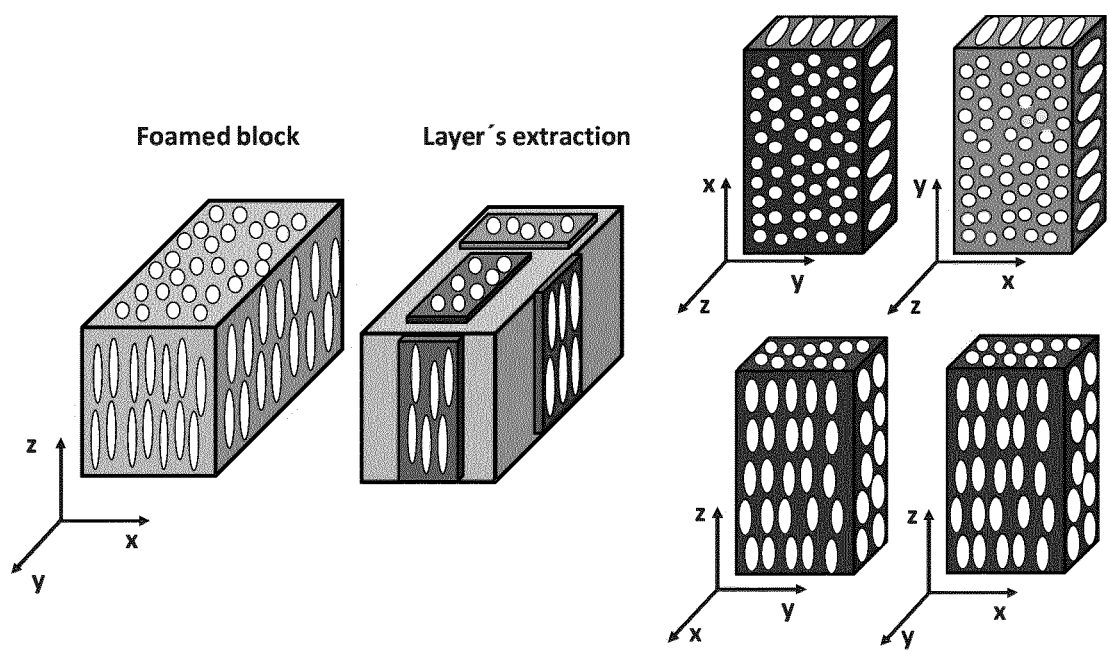
FIG. 8 is an illustration showing different layers generated by cutting a foam block according to an aspect of the disclosure.

FIG. 8 shows schematically how to obtain different layers of specifically oriented anisotropic foam cells by the cutting step (iv) above. Preferably, the first cutting plane is parallel to the x-y plane and the second cutting plane is parallel to the z-x plane and/or the z-y plane, and typically both being substantially perpendicular to the x-y plane.

In traditional foam making nucleating agents, such as talc, mica calcium carbonate, nanoclays, and the like, are typically used in order to increase cell nucleation. However, in the present disclosure, the inventors have found that by eliminating such nucleating agents, and thus rather promoting cell growth or a small number of large cells, improved anisotropic shaped cells can be achieved which are found to be most beneficial in the core arrangements described herein. Thus, in a preferred embodiment, the formulation is free of nucleating agents such as talc, mica calcium carbonate, and nanoclays.

The method of making absorbent articles 7,122 as described herein may comprise the steps of:
(i) providing an absorbent core as described herein;
(ii) laminating said absorbent core, directly or indirectly, between a liquid permeable topsheet and a liquid impermeable backsheet, preferably such that the first layer 2 is in direct or indirect contact with the topsheet and the second layer 3 is in direct or indirect contact with the backsheet, typically wherein the first and second layers 2,3 are not adhered together by a bonding substance, such as a hotmelt adhesive.

Absorbent cores 1 herein are particularly useful for providing directional flow of menses therethrough and preferably limit the amount of menses residues viewable on the first layer 2 when viewed from the body facing side thereof. This is achieved in a simple and cost effective way without complex and considerable foam formulation and processing requirements.

Test Methods

Relative density ($\rho_{rel}$):

It is defined as the density of the foamed material ($\rho_f$) divided by the density of the solid material before foaming ($\rho_s$). Density of foamed samples ($\rho_f$) is measured as described in ASTM D1622/D1622M-14. In this method samples with a defined geometry are cut from the foamed block and its dimensions and weight are obtained using a caliper with a precision of 0.01 mm and a balance with a precision of 0.01 mg. Density is obtained as the ratio between the mass and the volume of each sample. Density is determined in three different samples for each material, with a diameter of 30 mm and a height of 25 mm.

Porosity (P):

It is volume fraction (in percentage) of the gas phase within the material (e.g. the foam). It is calculated using the following equation (in other words also, 100 times, one minus the relative density):

$$P = 100\left(1 - \frac{\rho_f}{\rho_s}\right)$$

The density of the solid material for 100% open cell foam is measured by using gas picnometry technique following ASTM D6226-05 In this method the weight of the sample is measured using a balance with a precision of 0.01 mg. Then the volume of the solid phase is measured using a gas pycnometer, in our case we have used nitrogen gas for all the measurements. The equipment used is a gas pycnometer Accupyc II 1340 from Micromeritics. The density of the solid material is obtained as the ratio between the weight of the sample and the volume of the solid phase measured by the gas pycnometer. In the particular case of PU based foams the density of the solid phase was 1160 kg/m3.

Average Cell (or Pore) Size:

Three (3) samples of each foam layer are cut into squares of 5 by 5 mm in size. Each sample is vacuum coated with a gold thin layer (a few nm thick) and the cellular morphology of the foams is observed by Scanning Electron Microscopy (SEM) with a JEOL JSM-820 microscope. Each sample is examined by SEM on each of the planes xy, x+z, and yz (as shown schematically in the figures herein) by taking at least 3 SEM micrographs in random locations from each plane. An image analysis technique is then used according to and as described in "Characterization of the cellular structure based on user-interactive image analysis procedures" [Pinto J, Solorzano E, Rodriguez-Perez M A, and de Saja J A. *Journal of Cellular Plastics* 2013; 49(6):555-575.], herein incorporated by reference, for each of the SEM micrographs to determine the main characteristics of the cellular foam structure: average cell (por pore) size (ϕ), and average anisotropy ratio (R).

As it is indicated in the cited reference, the method gives quantitate results virtually identical to the standard method ASTM D3576-04 Standard Test Method for Cell Size of Rigid Cellular Plastics with the added benefit of providing a more detailed description of the cellular structure of the materials.

The average cell size and anisotropy ratio are measured for each plane of the foam (xy, xz and yz). In this way three averages cell sizes (one per plane) and three anisotropy ratios (one per plane) can be obtained for each foam. In the next paragraphs we explain how these parameters are measured for one plane. The description is for the xy plane but the same method is repeated for the other two planes.

Figure 9:
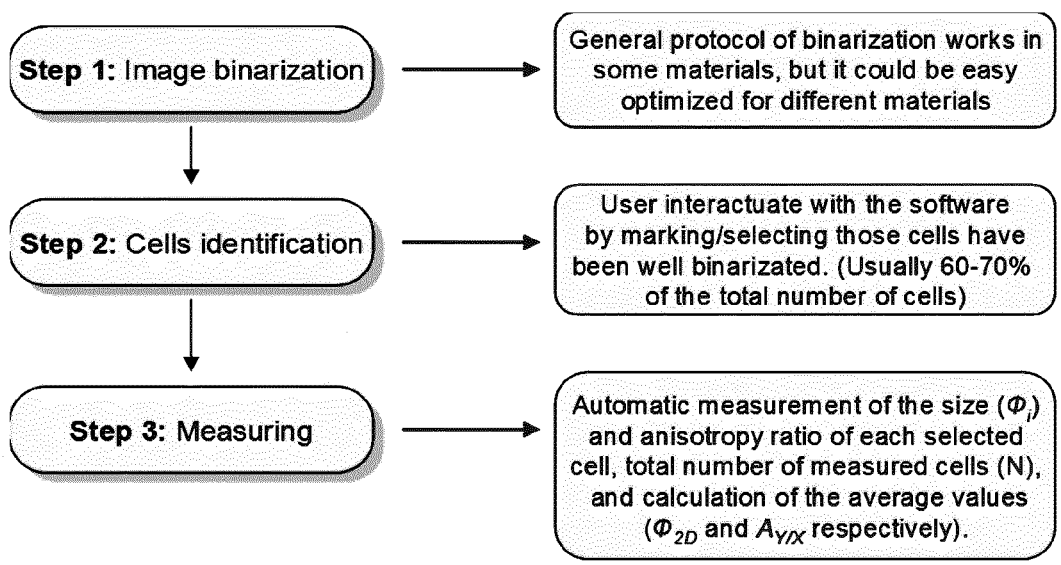
FIG. 9 is a flow diagram of a method used to measure the average cell size and the average anisotropy ratio, according to an aspect of the disclosure.
Figure 10:
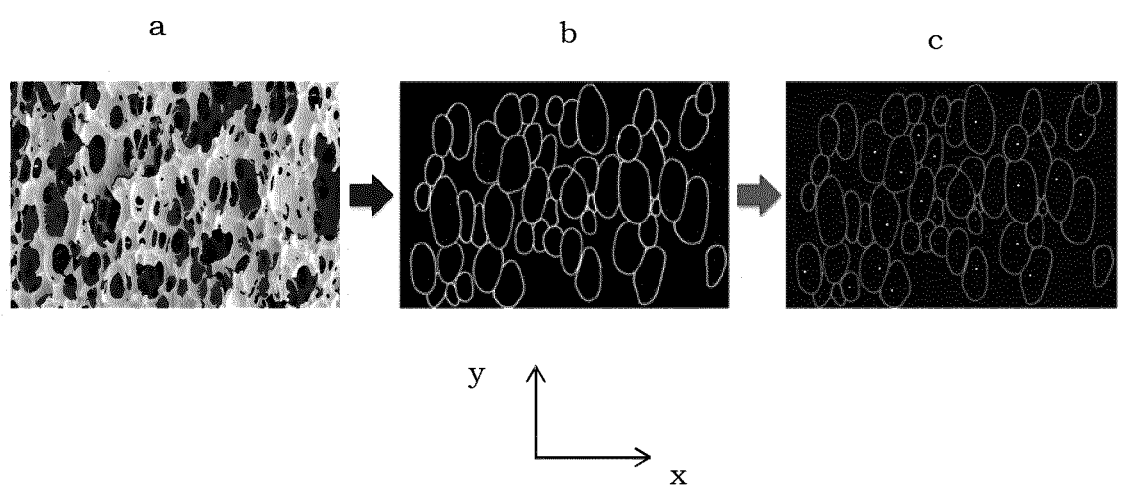
FIG. 10 exemplifies the micrograph processing: a) original SEM image; b) binarization of the image; and c) selection of the cells to measure the average cell size and the average anisotropy ratio according to the methods described herein.

A schematic flow diagram of the method is shown in FIG. 9, summarizing the description of the process. First step, is the binarization of the micrographs, in the general process the image contrast is enhanced and a median filter is applied to reduce the noise of the image and preserve edges, then a convolve filter is applied to obtain an image where the edges are revealed. From this a binary image of the cell walls is obtained (FIG. 10).

Every binarizated micrograph could present some defects, voids that are not cells, broken cell walls and incomplete cells in the image borders. These defects are source of inaccuracy for the cellular structure characterization if an automatic cell identification process is used. This is the reason why a user-interactive cell identification process is implemented. It basically consists in a user selecting/validating the cells with no binarization/border defects which subsequently will be measured (see FIG. 10-c, with selected cells having dots in the center).

This process allows to measure a significant number of cells, in images with an appropriate magnification (around 150-200 cells per image) it is possible to measure around a 60-70% of the cells.

Each selected cell is measured following this procedure: first the center of the cell is selected, Subsequently, from this point it measures the cell diameter in eight different directions (angles), obtaining the bidimensional cell size in eight different directions. From these measurements, the cell size of each single cell is obtained by averaging the eight values obtained. Anisotropy ratio of each single cell is measured as the ratio between the cell size (diameter of the cell) in the y direction of the image and the cell size (diameter of the cell) in the x direction.

Once the values of the cell size and the anisotropy ratio of each single cell is measured the average value of these parameters for the collection of n cells measured are obtained. These are the parameters denominated as Average cell (or pore) size and Average anisotropy ratio (R) herein.

For all the foams characterized herein the cell size and anisotropy ratio of a minimum of 200 cells are determined to obtain representative average values of both parameters.

Opacity:

A dispersion colorimeter is preferably used for determining the opacity of a sample material. A preferred dispersion colorimeter is available from BYK-Gardner GmbH, Geretsried, Germany, under Trade Name "BYK Gardner Color-Guide 45/0" (Cat. No. 6800).

The measurements should be conducted by using a light source "A" at a viewing angle of 2° (degrees). This dispersion colorimeter includes a light source for Illuminant A (i.e., an approximation of incandescent lamp having a correlated color temperature of about 3000 K), a flat table, a white standard plate, a standard black plate, a photo detector which includes a multi-celled photo-detector diode array, and a computer. The white and black standard plates are available from the same company under Cat. Nos. 6811 and 6810, respectively. In the measurement, the white standard plate is placed on the flat table. A sample material is put on the white standard plate in a flat state. The sample material is illuminated by the light source with an incident angle of 45°. The reflection light which is reflected from the sample material is received by the photo detector with a receiving angle of 0°. The reflection rate (Yw) of the reflection light is detected by the photo detector. Similarly, after the black standard plate is placed on the flat table, the sample material is put on the black standard plate in a flat state. The sample material is illuminated by the light source with an incident angle of 45°. The reflection light which is reflected from the sample material is received by the photo detector with a receiving angle of 0°. The reflection rate (Yb) of the reflection light is detected by the photo detector. The opacity (OP) is obtained by the following formula:

$$OP(\%) = (Yb/Yw) \times 100 \quad (1)$$

This process is repeated for one sample sheet material at least five times and the average value of the opacities (OP) measured is calculated and recorded by the colorimeter. The average value of the opacities measured is called the opacity of a sheet material.

EXAMPLES

Foam Sample Preparation:

The foamed samples are prepared by the reactive foaming process, that is, by reacting a mixture of two components: a hydrophilic isocyanate based prepolymer phase and water based component inside a mould (the ratio of the two components in the mixture is 1:1). The reaction of these two components promotes on the one hand, the generation of a gas phase, which expands the viscous mixture and constitute the interior of the cells in the final foam, and on the other hand, the subsequent polymerization of the PU-based solid phase which in the end constitutes the cell walls and struts of the foam. The foam expansion takes place in the z (height) direction of the mould.

The isocyanate based prepolymer phase used in this example is HYPOL™ which is the brand commercially available from Dow Chemical. Distilled water is used as the water phase. Water phase is pre-cooled at 15 C and the prepolymer is maintained at room temperature before the mixing process. Both components are poured inside a plastic container and thoroughly mixed by a shear mixer (IKA EUROSTAR 60) at a constant speed (1500 rpm) and for 10 seconds. Shortly after, the mixture is poured into the bottom of a prismatic mould with the following dimensions: 20 (height)×10 (width)×10 (thickness) cm, which restricts the expansion of the foam to the height direction. The reaction between both components, which is exothermic, starts, which implies the generation of the gaseous phase, the expansion of the viscous mixture and the polymerization of the solid phase. After about 120 seconds, or time enough to complete the reaction process, the foam fills completely the mold and becomes stable. A foamed block with the following dimensions is obtained: 20×10×10. The restriction of the expansion to one direction because of using a the previously described mould promotes the generation of anisotropic cellular structures in which cells are oriented parallel to the height direction of the foamed block.

The process to produce hydrophilic PU foam, as described here, leads to the presence of a water excess in the solid phase, hence, the foamed block obtained is subjected to drying in a convection oven at 70 C for a period of time until reaching a water content of less than 0.5% in the final foam (the water content in the foam is measured by gravimetry: weight of the foamed block before drying—weight of the foamed block after drying/weight of the foamed block before drying).

Capillarity Measurements:

For the capillarity measurements, the dried foamed block previously described are sliced into three different types of layers (EXAMPLE A, B and C), all of them with 0.2 cm in thickness, 20 cm in length and 5 cm in width, but extracted from different planes considering the coordinate system attributed to the foamed block as illustrated in FIG. 8 in which z represents the height of the foamed block and at the same time, the direction at which the cells are preferentially oriented.

Both, EXAMPLES A and B, are sliced from plane xy, although in EXAMPLE A, the length direction of the layer corresponds to the x direction of the foamed block, while in EXAMPLE B the length direction of the layer corresponds to the y direction of the foamed block. In both cases, the cells are oriented parallel to the layer thickness direction. EXAMPLE C is sliced from the two planes (xy and zx) parallel to the height direction of the foamed block (z) in such a way that cells are oriented parallel to the layer length direction (the results obtained for EXAMPLE C will represent the average of the two layers specified here).

The capillarity measurements are carried out by immersing the three EXAMPLES A-C into a recipient filled with synthetic blood (as formulated or prepared by SGS Courtray Laboratories (Oignies, France)) and by measuring the height reached by blood after diffusing against gravity (by holding each sample at 90°— and thus parallel to the direction of gravity) throughout the length direction of the layer for 300 seconds. In EXAMPLES A and B blood encounters cells which are oriented perpendicularly to the direction at which blood diffuses while in EXAMPLE C, blood encountered cells which are oriented parallel to the blood diffusion direction. Measurements are carried out in triplicate for each example.

The degree of orientation of the cells in the layers with respect to the direction at which blood diffuses is quantified by means of measuring the average anisotropy ratio (R) parameter (using the methods previously described) in three different layers corresponding to each one of the examples mentioned.

Figure 11:
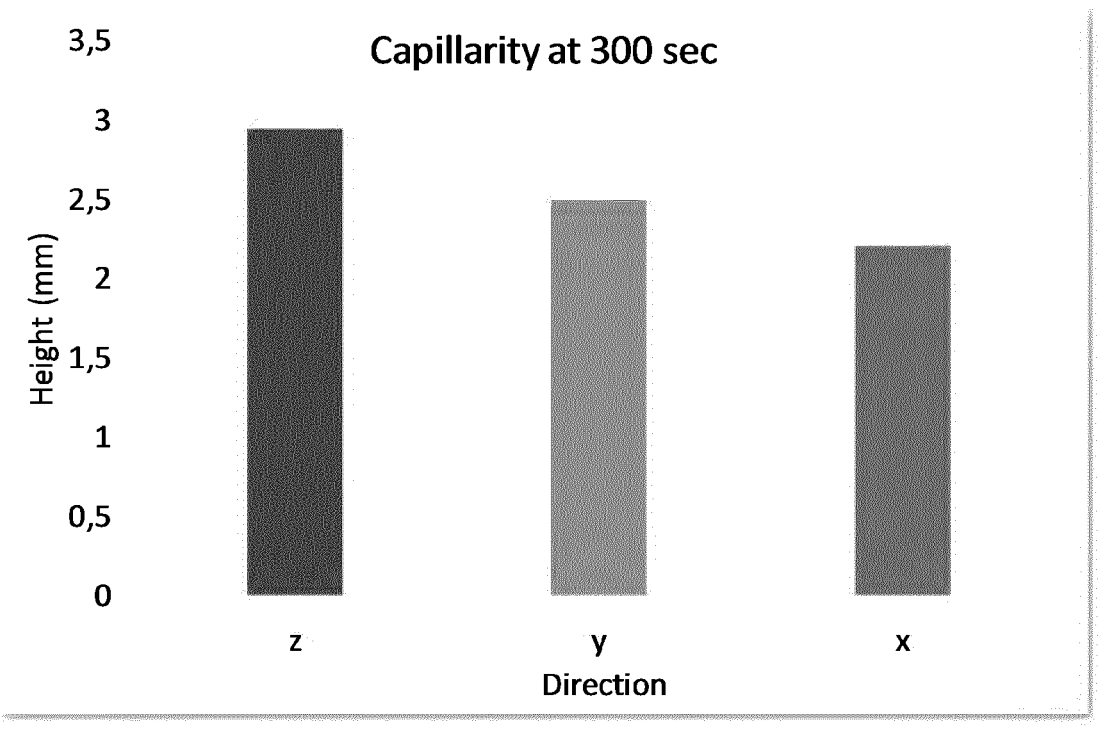
FIG. 11 is a graph showing capillarity of an anisotropic foam according to an aspect of the disclosure in three different directions.

TABLE 1 shows the results for each of the Examples A to C, and FIG. 11 further shows a graph summarizing the capillarity measurements.

|  | Example A | Example B | Example C |
|---|---|---|---|
| average anisotropy ratio R | 0.87 ± 0.05 | 1.14 ± 0.12 | 1.78 ± 0.07 |
| average cell size | 209.9 ± 10.7 | 194.2 ± 3.2 | 248.2 ± 20.3 |
| Capillarity (mm) | 2.2 ± 0.15 | 2.5 ± 0.08 | 2.9 ± 0.11 |

Table 1 (and FIG. 11) show improved capillarity along the axis of anisotropy for anisotropic foams.

Stress at 5% Strain:

The mechanical properties of foams with anisotropic cellular structures are directionally dependent. For this reason, the mechanical properties of the samples described in EXAMPLES A and C are measured under compression (75% of strain; strain rate: 10 s$^{-1}$ using a universal testing machine model 5.500R6025 Instron and employing the following procedure: the layers are placed between the compression plates of the testing machine and are compressed along the thickness direction of the layers in such a way that in EXAMPLE A, cells are oriented parallel to the compression direction and in EXAMPLE C, cells are oriented perpendicular to the compression direction.

Examples A and C are measured both in the dry state and in the wet state (after having absorbed blood) in order to evaluate how they are modified by the fact of absorbing blood.

TABLE 2 shows the stress results for each of the Examples A and C.

|  | Example A | Example C |
|---|---|---|
| Stress at 5% Strain (kPa) dry | 2.2 ± 0.32 | 1.8 ± 0.12 |
| Stress at 5% Strain (kPa) wet | 1.6 ± 0.11 | 1.6 ± 0.21 |

It is desirable for materials to have at least a stress value greater than that identified and described herein but not too high in order to avoid other disadvantages such as increased overall stiffness of the product. As can be seen from table 2, Example C has a stress greater than the minimum level identified and described herein but very close thereto thus providing a more comfortably perception to the user. It is also interesting to note that the mechanical resistance of the product is reduced when the material is in the wet state improving them the comfortability.

Acquisition Time:

Examples A and C are measured by the acquisition time tests which evaluates the speed at which a determined layer of the absorbent core absorbs blood. A holed cylinder made of metal is placed above the upper surface of the layer which is tested. A determined amount of blood (4 ml) (having the same composition as previously described and used in examples herein) is poured at a constant flux rate throughout the central hole of the cylinder and the time required for the layer to absorb it completely is registered. This procedure is repeated two times hence, each one of them is denominated as T1 and T2. The acquisition time is the sum of the two times: T1+T2.

The fluid used in this method is artificial blood, as formulated or prepared by SGS Courtray Laboratories (Oignies, France). This fluid has a viscosity of 7-8 cPa (Target 7.5 cPA) measured at a temperature of 21° C. using a falling ball type viscosimeter (Category number V-2200, size 2, K value 3.3) with a glass ball.

TABLE 3 shows the acquisition time results for each of Examples A to C with sample C showing reduced acquisition time.

|  | Example A | Example C |
|---|---|---|
| Acquisition time (seconds) | 81.9 ± 4.1 | 71.5 ± 2.3 |

Rewet:

Example D is made by combining a first layer (EXAMPLE A) and a second layer (EXAMPLE C) both having anisotropic cells but oriented perpendicular to each other and according to cores of the present disclosure.

Example E is a fluff comprising core of the prior art (Ultra fluff towel with a core comprising cellulosic fluff fibers and super absorbent particles, manufactured by Ontex®) commercially available by Ontex bvba.

Example F is a foam core according to Always® Infinity pads commercially available by the Procter & Gamble Company.

The EXAMPLES D, E and F are subjected to the "rewet test" as defined by SGS Courtray Laboratories (POA/DF7-DF8: Simulation test sitting and standing position in feminine hygiene) which measures the blood retention capacity of the absorbent core when it is subjected to different stress conditions: standing (less demanding) or sitting (more demanding). The test liquid used is artificial blood as formulated or prepared by SGS Courtray Laboratories, as described in examples A and C.

TABLE 4 shows the rewet results for each of Examples D to F

|  | Example D | Example E | Example F |
|---|---|---|---|
| REWET (g) | 0.00 ± 0.0 | 1.04 ± 0.08 | 2.08 ± 0.12 |

Surprisingly, from table 4 it is shown that Example D provide for exceptional performance over both fluff and foam cores of the prior art.

Standard Deviation (SD) Test:

The EXAMPLES D, E and F of the present invention are subjected to the "standard deviation test" which indirectly measures the size of the blood spot on the acquisition layer (2) by measuring the ratio between the area occupied by the blood spot seen from the upper view and the total area of the absorbent core (the value is given in percentage).

TABLE 5 shows the standard deviation test for each of Examples D to F

|        | Example D    | Example E    | Example F    |
|--------|--------------|--------------|--------------|
| SD (%) | 44.7 ± 2.2   | 87.4 ± 3.4   | 47.7 ± 1.1   |

Surprisingly, from table 5 it is shown that Example D performs better than foam products of the prior art and significantly better than fluff products of the prior art.

It is supposed that the present invention is not restricted to any form of realization described previously and that some modifications can be added to the presented example of fabrication without reappraisal of the appended claims.

The invention claimed is:

1. An absorbent core (1) for an absorbent article, the absorbent core comprising at least two layers (2,3), each layer having a width (w) and a length (l) along a first plane and a thickness (t) extending perpendicular thereto, wherein said layers (2,3) are arranged in facing relationship along said first plane, and wherein said layers (2,3) comprise a polymeric foam having an open cell and interconnected porous structure characterized in that the first layer (2) and the second layer (3) comprise an anisotropic cell structure having an axis of anisotropy (4,5) extending substantially parallel to a longest length of a plurality of substantially neighbouring cells (6), in that the axis of anisotropy (5) of the second layer (3) extends substantially perpendicular to said thickness (t) and parallel to said first plane, and in that the axis of anisotropy (4) of the first layer (2) is substantially perpendicular to the axis of anisotropy (5) of the second layer (3).

2. An absorbent core (1) according to claim 1 wherein the first layer (2) is positioned above the second layer (3) such that when said absorbent core (1) is incorporated into an absorbent article, said first layer (2) is closer to a body facing side of the absorbent article than said second layer (3).

3. An absorbent core (1) according to claim 1 wherein the axis of anisotropy (4) of the first layer (2) is substantially perpendicular to the first plane and crosses said first and second layers (2,3).

4. An absorbent core (1) according to claim 1 wherein the axis of anisotropy (5) of the second layer (3) extends along the length (l) of said second layer (3) without crossing the first layer (2).

5. An absorbent core (1) according to claim 1 wherein the foam open cells (6) have an average anisotropy ratio R of greater than 1, as measured according to the method described herein.

6. An absorbent core (1) according to claim 1 wherein the foam comprises a hydrophilic polymer foam.

7. An absorbent core (1) according to claim 6 wherein the hydrophilic polymer foam is selected from the group consisting of polyurethane; poly vinyl alcohol (PVA); polyolefins selected from the group consisting of low-density polyethylene (LDPE), ethylene-vinyl acetate (EVA), ethylene butyl acrylate (EBA), and mixtures thereof; open cell silicone foams; and mixtures thereof.

8. An absorbent core (1) according to claim 1 wherein the foam open cells (6) have an average anisotropy ratio R of from 1.1 to 3.5, as measured according to the method described herein.

9. An absorbent core (1) according to claim 1 wherein the foam open cells (6) have an average anisotropy ratio R of from 1.2 to 3.3, as measured according to the method described herein.

10. An absorbent core (1) according to claim 1, wherein the absorbent core further comprises cellulosic fibers and/or super absorbent polymer particles.

11. A method of making an absorbent core (1) according to claim 1, the method comprising the steps of:
    (i) providing a mixture comprising one or more polymers;
    (ii) placing said mixture in a mould arranged such that cell growth is promoted along an axis during a foaming step to provide a foam comprising an anisotropic cell structure;
    (iii) forming a foam block by solidifying said mixture;
    (iv) demoulding the foam block;
    (v) generating a first layer (2) and/or second layer (3) by cutting the foam block along a first cutting plane and a second cutting plane perpendicular to the first cutting plane to generate the second layer (3) and/or first layer (2);
    (vi) optionally repeating step (v) until substantially the entire foam block is cut into layers; and
    (vi) assembling the first and second layers (2,3) in facing relationship.

12. A method according to claim 11 wherein the mixture is free of nucleating agents.

13. An absorbent article (7) comprising an absorbent core (1) according to claim 1.

14. An absorbent article (7) according to claim 13, wherein said absorbent article is selected from the group consisting of sanitary napkins and towels for feminine care.

15. An absorbent article (7) according to claim 13 wherein the absorbent core (1) comprises one or more interconnected macro channels (10) at least on an upper surface of the first layer (2), said upper surface being opposite the second layer (3), and extending at least a portion of the length (l) and width (w) of said first layer (2).

16. An absorbent article (7) comprising an absorbent core (1) according to claim 1, wherein the absorbent article (7) comprises a liquid permeable topsheet (8) and a liquid impermeable backsheet (9) with said absorbent core (1) being sandwiched therebetween.

17. An absorbent article (7) according to claim 16 wherein the topsheet (8) or the uppermost surface of the first layer (2) closest to said topsheet (8) comprises a coloured area comprising a colour pigment imparting a hue having an ω angle measured in the CIELAB colour scale of from 135° to 315°.

18. An absorbent article (7) according to claim 17 wherein said coloured area extends across an entire surface of the topsheet (8) or the first layer (2); or is located in a central portion of said absorbent article (7) and distal from perimeter edges thereof.

19. An absorbent article (7) according to claim 18 wherein the coloured area is substantially circumscribed by a non-coloured area.

20. An absorbent article (7) according to claim 17, wherein said coloured area has an opacity of at least 20%.

21. A method of making an absorbent article (7) according to claim 16, the method comprising the steps of:
    (i) providing an absorbent core according to claim 1;
    (ii) laminating said absorbent core between the liquid permeable topsheet and the liquid impermeable backsheet.

22. A method of making an absorbent article (7) according to claim 21, wherein the laminating step (ii) is such that the first layer (2) is in direct or indirect contact with the topsheet and the second layer (3) is in direct or indirect contact with the backsheet.

\* \* \* \* \*